United States Patent
Brubaker et al.

(10) Patent No.: US 6,756,049 B2
(45) Date of Patent: Jun. 29, 2004

(54) SUSTAINED RELEASE DRUG DELIVERY DEVICES

(75) Inventors: Michael J. Brubaker, Fort Worth, TX (US); Ramesh Krishnamoorthy, Apex, NC (US); Michael A. Lesczynski, Honeoye Falls, NY (US); Thomas F. Natalie, Rochester, NY (US); Pavlos Papadopoulos, Antioch, IL (US); Steven B. Renner, Rochester, NY (US); Santos Viscasillas, Tampa, FL (US); E. Allen Martin, Charlotte, NC (US); Jason Paul Shropshire, Huntersville, NC (US)

(73) Assignee: Bausch & Lomb Incorporated, Rochester, NY (US)

( * ) Notice: Subject to any disclaimer, the term of this patent is extended or adjusted under 35 U.S.C. 154(b) by 25 days.

(21) Appl. No.: 10/023,391

(22) Filed: Dec. 17, 2001

(65) Prior Publication Data

US 2002/0110591 A1 Aug. 15, 2002

Related U.S. Application Data

(60) Provisional application No. 60/259,135, filed on Dec. 29, 2000.

(51) Int. Cl.[7] .............................. A61F 2/00; A61F 9/00; A61K 9/00; A61K 9/20; A61K 9/28
(52) U.S. Cl. ....................... 424/428; 424/400; 424/422; 424/423; 424/427; 424/464; 424/468; 424/474; 424/475
(58) Field of Search ................................ 424/400, 423, 424/424, 427, 428, 464, 468, 474, 475

(56) References Cited

U.S. PATENT DOCUMENTS

| 3,416,530 | A |   | 12/1968 | Ness ......................... 128/260 |
| 3,618,604 | A |   | 11/1971 | Ness ......................... 128/260 |
| 3,946,734 | A |   | 3/1976 | Dedrick et al. ............. 128/260 |
| 4,014,335 | A |   | 3/1977 | Arnold ....................... 128/260 |
| 4,657,543 | A | * | 4/1987 | Langer et al. .............. 604/891 |
| 4,929,233 | A |   | 5/1990 | Roth et al. .................. 604/131 |
| 5,378,475 | A | * | 1/1995 | Smith et al. ................ 424/473 |
| 5,773,019 | A | * | 6/1998 | Ashton et al. .............. 424/423 |
| 5,902,598 | A |   | 5/1999 | Chen et al. ................. 424/423 |
| 6,001,386 | A |   | 12/1999 | Ashton et al. .............. 424/423 |
| 6,004,582 | A |   | 12/1999 | Faour et al. |
| 6,113,938 | A |   | 9/2000 | Chen et al. |
| 6,303,144 | B1 |   | 10/2001 | Omura |
| 6,375,972 | B1 | * | 4/2002 | Guo et al. .................. 424/473 |
| 6,413,540 | B1 | * | 7/2002 | Yaacobi ...................... 424/427 |

FOREIGN PATENT DOCUMENTS

| EP |   | 0861659 | A1 | 9/1998 | ............ A61K/9/52 |
| WO | WO 98/42317 |   |   | 10/1998 |   |
| WO | WO 00/48660 |   |   | 8/2000 |   |
| WO | WO 01/80825 |   |   | 11/2001 |   |
| WO | WO 02/53128 |   |   | 7/2002 |   |
| WO | WO 02/53129 |   |   | 7/2002 |   |
| WO |   | 02/056863 |   | 7/2002 | ............ A61K/9/00 |

OTHER PUBLICATIONS

Controlled Drug Delivery (Part I, Xue Shen Wu, PhD, pp. 32, 33, 44–46, 63, 66 & 67) Technomic Publishing Co., Inc., 1996.

Controlled Drug Delivery Systems, Xue Shen Wu, PhD., Technomic Publishing Co, 1996.

* cited by examiner

*Primary Examiner*—Gollamudi S. Kishore
*Assistant Examiner*—Simon J. Oh
(74) *Attorney, Agent, or Firm*—Glenn D. Smith; Denis A. Polyn (57) ABSTRACT

The present invention is directed to an improved sustained release drug delivery device comprising a drug core, a unitary cup, and a permeable plug.

37 Claims, 3 Drawing Sheets

SUSTAINED RELEASE DRUG DELIVERY DEVICES

This application claims the benefit of Provisional Application No. 60/259,135 filed Dec. 29, 2000.

FIELD OF THE INVENTION

The present invention relates to an improved device and method for delivering drug directly to the interior portions of the body of a mammalian organism, such as to the eye. The method includes administration of an agent effective in obtaining a desired diagnostic effect or local or systemic physiological or pharmacological effect by inserting in a desired location in the body of a mammalian organism a sustained release drug delivery device.

BACKGROUND

Over the years, various drugs have been developed to assist in the treatment of a wide variety of ailments and diseases. However, in many instances such drugs are not capable of being administered either orally or intravenously without the risk of various detrimental side effects.

CMV retinitis is a disease that is characterized by inflammation of the retina caused by infection with cytomegalovirus. CMV retinitis is one of the most common causes of sight-threatening infections among people with HIV. The symptoms include loss of visual acuity, blind spots, and the loss of peripheral vision. Left untreated, CMV retinitis can lead to blindness.

Intravenous ganciclovir (GCV) is effective in the treatment of CMV retinitis in AIDS patients, but bone marrow toxicity limits its usefulness. Continuous maintenance GCV therapy is necessary to prevent progression or recrudescence of the disease, but despite maintenance therapy a significant number of patients experience a relapse during treatment. Additionally, there are other risks and problems associated with systemic GCV administration.

Intravitreal GCV injections administered once or twice weekly have resulted in temporary remission of CMV retinitis in AIDS patients. Intravitreal GCV injections may provide a higher intraocular drug concentration than systemic therapy and reduce the incidence of neutropenia. However, current treatment of CMV retinitis in AIDS patients is clearly suboptimal. Ganciclovir is virustatic and thus disease inhibition requires maintenance drug administration.

A more detailed explanation of the use of intravenous of GCV and intravitreal injections of GCV can be found in U.S. Pat. No. 5,902,598, herein incorporated in its entirety by reference. A discussion of the difficulties associated with the systemic therapy of cyclosporine A in the treatment of uveitis can be found in U.S. Pat. Nos. 5,773,019 and 6,001,386, herein incorporated in their entirety by reference.

Accordingly, there exists a strong need for the elimination of the undesirable physiological problems associated with GCV treatment of CMV retinitis, while maintaining the advantageous properties of this treatment. Although delivering the drug locally with injections may minimize the systemic toxicity of GCV, repeated injection is not a practical mode of administration.

Due to the risks that certain drugs impose, researchers have developed systems for administering such drugs to aid in the treatment of these ailments and diseases. A general discussion of drug delivery control systems is provided in Controlled Drug Delivery (Part I), Xue Shen Wu, Ph.D. pp32, 33, 44–46, 63, 66, and 67 (Technomic Publishing Co. Inc., 1996), the entire contents of which are incorporated herein by reference. The systems have been designed largely to reduce and to control the release rate of incorporated drugs. However, these systems fail to achieve the advantages claimed by the present invention.

For example, U.S. Pat. No. 4,014,335 to Arnold, relates to various ocular inserts that act as a deposit or drug reservoir for slowly releasing a drug into the tear film for prolonged periods of time. These inserts are fabricated as a three-layer laminate of flexible polymeric materials that are biologically inert, non-allergenic, and insoluble in tear fluid. To initiate the therapeutic programs of these devices, the ocular inserts are placed in the cul-de-sac between the sclera of the eyeball and the eyelid for administering the drug to the eye. Multiple layer laminate systems can present a challenge to reproducibly manufacture and are more difficult to produce by large-scale manufacturing procedures.

The device of U.S. Pat. No. 3,416,530 is manufactured with a plurality of capillary openings that communicate between the exterior of the device and the interior chamber generally defined from a polymeric membrane. While the capillary openings in this construction are effective for releasing certain drugs to the eye, they add considerable complexity to the manufacture of the device because it is difficult to control the size of these openings in large-scale manufacturing using various polymers.

U.S. Pat. No. 3,618,604 describes a device that does not involve such capillary openings, but instead provides for the release of the drug by diffusion through a polymeric membrane. The device, as disclosed in a preferred embodiment, comprises a sealed container with the drug contained in an interior chamber. Nonetheless, as described in U.S. Pat. No. 4,014,335, certain problems have been identified with such devices such as the difficult task of sealing the margins of the membrane to form the container. In addition, stresses and strains introduced into the membrane walls from deformation during manufacturing of those devices may cause the reservoir to rupture and leak.

The above described systems and devices are intended to provide sustained release of drugs effective in treating patients at a desired local or systemic level for obtaining certain physiological or pharmacological effects. However, there are many disadvantages associated with their use, including the fact that it is often difficult to obtain the desired release rate of the drug.

The need for a better release system is especially significant in the treatment of CMV retinitis. Thus, there remains a long-felt need in the art for an improved device for providing sustained release of a drug to a patient to obtain a desired local or systemic physiological or pharmacological effect.

Prior to the development of the present invention, there was developed a drug delivery device that ameliorated many of the problems associated with sustained release drug delivery. The device, which is disclosed in U.S. Pat. No. 5,378,475 (incorporated herein by reference in its entirety), included a first coating essentially impermeable to the passage of the effective agent and a second coating permeable to the passage of the effective agent. In the device, the first coating covered at least a portion of the inner core; however, at least a small portion of the inner core is not coated with the first coating layer. The second coating layer essentially completely covers the first coating layer and the uncoated portion of the inner core. The portion of the inner core which is not coated with the first coating layer allows passage of the agent into the second coating layer thus allowing controlled release.

While the devices described in U.S. Pat. No. 5,378,475 solve many of the aforementioned problems pertaining to drug delivery, the devices and the method of making the devices are not without some problems. In particular, polymers suitable for coating the inner core are frequently relatively soft and technical difficulties can arise in production of uniform films. This is especially true when attempting to coat non-spherical bodies with edges (such as a cylindrical shape). In such cases, relatively thick films must be applied to achieve uninterrupted and uniform coatings, which adds significant bulk to the device. Thus, the devices tend to be larger than necessary as a result of the thickness needed to seal the ends of the inner core. In addition to adding bulk, multiple layer devices are more difficult to manufacture reproducibly and are more difficult to produce by large-scale manufacturing procedures. Often devices such as these require manual assembly that is time consuming, limits available supply, and adds variability.

U.S. Pat. No. 5,902,598 also presents solutions to some of the problems associated with manufacturing small devices. The device in U.S. Pat. No. 5,902,598 includes a third permeable coating layer that essentially completely covers the device. While the third coating layer improves the structural integrity of the device and helps to prevent potential leakage, some manufacturing difficulties can limit scaled up manufacturing. For example, consistent application of the outermost coating layer and reproducibility in manufacturing can be problems with designs which require manual assembly, a significant number of steps in the assembly process, or outer dip coatings.

In addition, depending on the materials selected for the outermost coating layer of the devices in U.S. Pat. Nos. 5,902,598 and 5,378,475, there may exist a need to cure the entire device including the agent. Depending on the amount of curing required and the agents used, in some applications this could result in undesirable degradation of the active.

The problem of device size is extremely important in the design of devices for implantation into the limited anatomical spaces such as small organs like the eye. Larger devices require more complex surgery to both implant and remove. The increased complexity can result in complication, longer healing or recovery periods, and potential side effects (e.g. increased chance of astigmatism). Further, the extra polymer required to achieve a uniform coating reduces the potential internal volume of the implant and hence limits the amount of drug that can be delivered, potentially limiting both efficacy and duration.

It would, therefore, be desirable to have a structurally stable device that can be reproducibly manufactured and manufactured by commercial techniques. As a result of all of the above, there remains a long felt need in the art for an improved device for providing sustained release of a drug to a mammalian organism to obtain a desired local or systemic physiological or pharmacological effect, especially for ocular use.

SUMMARY OF THE INVENTION

The sustained release drug delivery device according to the first embodiment of the present invention comprises:

a) a drug core comprising a therapeutically effective amount of at least one agent effective in obtaining a diagnostic effect or effective in obtaining a desired local or systemic physiological or pharmacological effect;

b) a unitary cup essentially impermeable to the passage of said agent that surrounds and defines an internal compartment to accept said drug core, said unitary cup comprising an open top end with at least one recessed groove around at least some portion of said open top end of said unitary cup; and c) a permeable plug which is permeable to the passage of said agent, said permeable plug is positioned at said open top end of said unitary cup wherein said groove interacts with said permeable plug holding it in position and closing said open top end, said permeable plug allowing passage of said agent out of said drug core, through said permeable plug, and out said open top end of said unitary cup.

In accordance with another embodiment of the present invention is a sustained release drug delivery device comprising:

a) a drug core comprising at least one agent effective in obtaining a diagnostic effect or effective in obtaining a desired local or systemic physiological or pharmacological effect;

b) a unitary cup essentially impermeable to the passage of said agent that surrounds and defines an internal compartment to accept said drug core, said unitary cup comprising an open top end and at least one lip around at least a portion of said open top end of said unitary cup; and c) a permeable plug permeable to the passage of said agent positioned at said open top end of said unitary cup wherein said lip interacts with said permeable plug holding it in position and closing said open top end, said permeable plug allowing passage of said agent out of said drug core, through said permeable plug, and out said open top end of said unitary cup.

This invention is also directed to a method for providing controlled and sustained administration of an agent effective in obtaining a desired local or systemic physiological or pharmacological effect comprising inserting in a desired location in the body of a mammalian organism sustained release drug delivery devices of the first and second embodiments of the present invention.

A method of manufacture of a sustained release drug delivery device according to the present invention comprises:

a) manufacturing a drug core comprising at least one agent effective in obtaining a diagnostic effect or effective in obtaining a desired local or systemic physiological or pharmacological effect;

b) providing a unitary cup essentially impermeable to the passage of said agent that surrounds and defines an internal compartment to accept said drug core, said unitary cup comprising an open top end with at least one recessed groove around at least some portion of said open top end of said unitary cup;

c) inserting said drug core into said unitary cup; and d) filling a material which is permeable to the passage of said agent into said open top end of said unitary cup, allowing said material to solidify thereby forming a permeable plug wherein said groove interacts with said permeable plug holding it in position and closing said open top end, said permeable plug allowing passage of said agent out of said drug core, through said permeable plug, and out said open top end of said unitary cup.

The present invention is further directed to a method of manufacturing a sustained release drug delivery device comprising:

a) manufacturing a drug core comprising at least one agent effective in obtaining a diagnostic effect or effective in obtaining a desired local or systemic physiological or pharmacological effect;

b) providing a unitary cup essentially impermeable to the passage of said agent that surrounds and defines an internal compartment to accept said drug core, said unitary cup comprising an open top end with at least one lip extending around at least a portion of the said open top end of said unitary cup;

c) inserting said drug core into said unitary cup; and d) filling a material which is permeable to the passage of said agent into said open top end of said unitary cup, allowing said material to solidify thereby forming a permeable plug wherein said lip interacts with said permeable plug holding it in position and closing said open top end, said permeable plug allowing passage of said agent out of said drug core, through said permeable plug, and out said open top end of said unitary cup.

BRIEF DESCRIPTION OF THE DRAWINGS

The drawings, which are not drawn to scale, are set forth to illustrate various embodiments of the invention. The drawings are as follows.

DETAILED DESCRIPTION OF THE INVENTION

The inventors have unexpectedly discovered a sustained release drug delivery device that because of its unitary cup and permeable plug design is structurally stabile and can be more easily and reproducibly manufactured than current designs that are known in the art.

In one preferred embodiment, the device includes an impermeable unitary cup made of silicone with an integral suture tab, the unitary cup acts as a reservoir for a drug core containing an agent such as fluocinolone acetonide. A hole through the proximal end of the suture tab enables a suture to be used for securing the device. The open end of the unitary cup has lips extending inwardly around a portion of the top open end of said cup. A permeable polymer solution of 10% polyvinyl alcohol (PVA) is filled in the recess above the drug core. The PVA solution is allowed to dry. The device is cured for 60 minutes at 135–140° C. The PVA is sufficiently rigid to maintain its shape and the integrity of the device and thereby forming a permeable plug such that the lips interact with the plug holding it in position and closing the open top end. Together the cup with lips and the permeable plug act as a reservoir surrounding the drug core and keeping it in place.

The expression "agent" as used herein broadly includes any compound, composition of matter, or mixture thereof that can be delivered from the device to produce a beneficial and useful result.

The term "impermeable" refers to a material that is sufficiently impermeable to environmental fluids as well as ingredients contained within the delivery device, such that the migration of such fluids and ingredients into or out of the device through the impermeable material is so low as to have substantially no adverse impact on the function of the device.

The term "permeable" refers to a material that is capable of being passed through or permeated. Permeating includes passing through openings, holes, pores, or intersections.

The term "drug core" refers to any drug supply, drug depot, drug in suspension, reservoir or drug matrix. It includes one or more agents necessary to obtain the desired diagnostic effect or local or systemic physiological or pharmacological effect. It includes any excipients, suspending agents, or binders. Reference may be made to any standard pharmaceutical textbook such as Remington's Pharmaceutical Sciences. The drug core can be in liquid form, solid form, in dispersion, or any other form known in the art. Solid dose includes all conventional solid dose forms known in the art including tablets and pellets. Dispersions include all conventional forms known in the art, such as liquid in liquid dispersions and solid in liquid dispersions.

The expression "passageway" as used herein includes an aperture, orifice, or bore sufficient to allow the agent to pass through. The passageway can be formed by mechanical procedures such as erosion, laser, or molding; and chemical procedures.

Referring to the drawing figures, like reference numerals designate identical or corresponding elements throughout the several figures.

Figure 1:
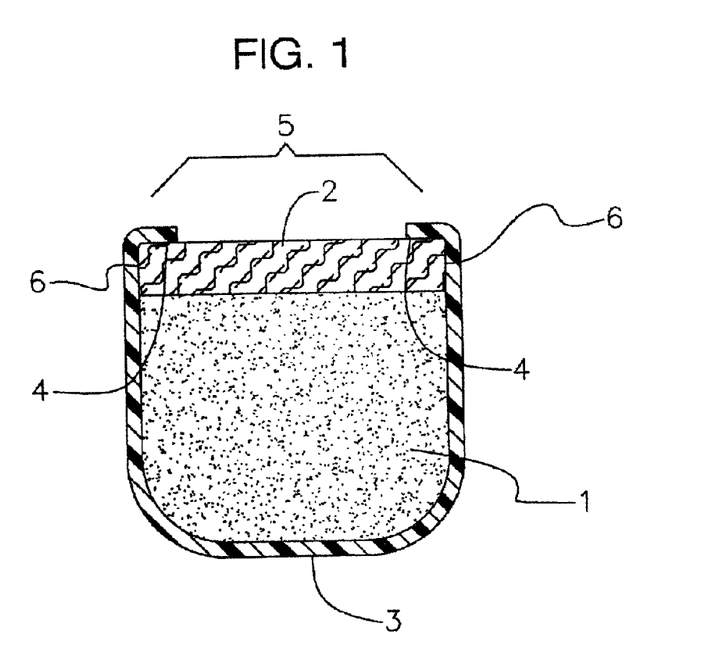
FIG. 1 of the present invention is an enlarged cross-sectional view down the center of one embodiment of the sustained release drug delivery device showing a unitary cup with a lip extending inward around some portion of the open top end of the cup, a permeable plug, the cup and plug acting as a reservoir for the drug core.

Turning now to the drawings in detail, which examples are not to be construed as limiting, one embodiment of a device is indicated in FIG. 1. While the device shown in FIG. 1 is generally U like in shape, the cup can be any open container or bowl of any shape. FIG. 1 is a cross sectional view of a drug delivery device in accordance with the present invention. FIG. 1 includes an impermeable unitary cup 3 containing a drug core 1 comprising an agent, the cup 3 has lips 4 extending inward around the open top end 5 of the cup 3; and a permeable plug 2 formed of a material permeable to the passage of agent contained in the drug core 1. The permeable plug 2 is positioned in the recess between the top of the drug core 1 and below the lips 4 such that the lips 4 interact with the permeable plug 2 holding it in position and closing the open top end 5 of the cup 3.

The lips 4 are the same impermeable material as the unitary cup 3 and protrude inwardly from the top open end 5 of the cup 3. The cup 3 and lips 4 are formed in a single unitary design to provide structural integrity to the device and facilitate manufacturing and handling. The lips 4 are designed to hold the plug 2 in place during use. They can vary in size or shape. The lips 4 of the present invention include nubs, tabs, ridges, and any other raised or protruding member.

The permeable plug 2 can be formed in the unitary cup by filling the permeable material in the device in one step, such as injecting a solution of PVA. The permeable plug 2 can be formed to various dimensional specifications which can be used to control diffusion properties to achieve a desired release rate. For example, changing the amount of the permeable material filled into the cup can vary the thickness of the permeable plug. The same unitary cup and lips design can be used for implants with a variety of release rates making it possible to use a single manufacturing line or type of equipment. Thus, the present invention allows for ease of construction by more standard manufacturing techniques into devices with different release rates.

Together the cup 3 with lips 4 and the permeable plug 2 act as a reservoir surrounding the drug core 1 and keeping it in place. The agent diffuses out of the drug core 1, through the permeable plug 2, and out the open top end 5. The permeable plug 2 has substantially the same radial extent as the cup 3, so that the only diffusion pathway is out of the plug 2 and not around the sides 6. Glue or other adhesion means can be employed to further bond the plug to the cup.

The invention further relates to a method for treating a mammalian organism to obtain a desired local or systemic physiological or pharmacological effect. The method includes administering the sustained release drug delivery device to the mammalian organism and allowing the agent effective in obtaining the desired local or systemic physiological or pharmacological effect to pass through the plug 2. The term "administering", as used herein, means positioning, inserting, injecting, implanting, or any other means for exposing the device to a mammalian organism. The route of administration depends on a variety of factors including type of response or treatment, type of agent, and the preferred site of administration. However, the preferred method is to insert the device into the target organ. In ocular applications, more preferably through a surgical procedure followed by suturing the device in place.

Figure 2:
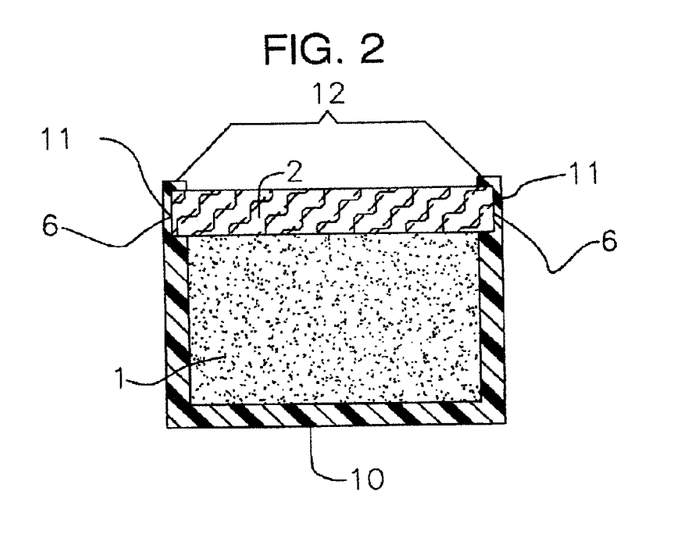
FIG. 2 of the present invention is an enlarged cross-sectional view down the center of another embodiment of the sustained release drug delivery device showing a unitary cup with a recessed groove around some portion of the inside of the open top end of the cup, a permeable plug, the cup and plug acting as a reservoir for the drug core.

FIG. 2 illustrates an enlarged cross sectional view down the center of a sustained release drug delivery device in accordance with the present invention. FIG. 2 includes an impermeable unitary cup 10 containing a drug core 1 comprising an agent, the cup 10 has a recessed groove 11 around the inside of the open top end 12 of the cup 10; and a permeable plug 2 formed of a material permeable to the passage of agent contained in the drug core 1. The permeable plug 2 is positioned such that the groove 11 interacts with the permeable plug 2 holding it in position and closing the open top end 12 of the cup 10.

Together the cup 10 with the groove 11 and the permeable plug 2 act as a reservoir surrounding the drug core 1 and keeping it in place. The agent diffuses out of the drug core 1, through the permeable plug 2, and out the open top end 12. The permeable plug 2 has substantially the same radial extent as the groove 11, so that the only diffusion pathway is out of the plug 2 and not around the sides 6. Glue or other adhesion means can be employed to further bond the plug to the cup.

Figure 3:
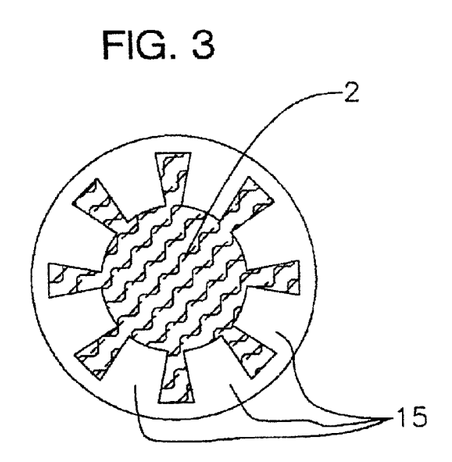
FIG. 3 of the present invention is an enlarged top view of another embodiment of the sustained release drug delivery device showing a unitary cup with a plurality of lips extending inward around at least a portion of the open top end of the cup, a permeable plug, the cup and plug acting as a reservoir for the drug core.

FIG. 3 is an enlarged top view of another exemplary embodiment of a sustained release drug delivery device of the present invention. The view in FIG. 3 is the top of a unitary cup comprising a plurality of lips 15 extending inwardly around the open top end of the cup. The permeable plug 2 is held in place by the lips 15 extending inwardly around the top open end of the cup.

Figure 4:
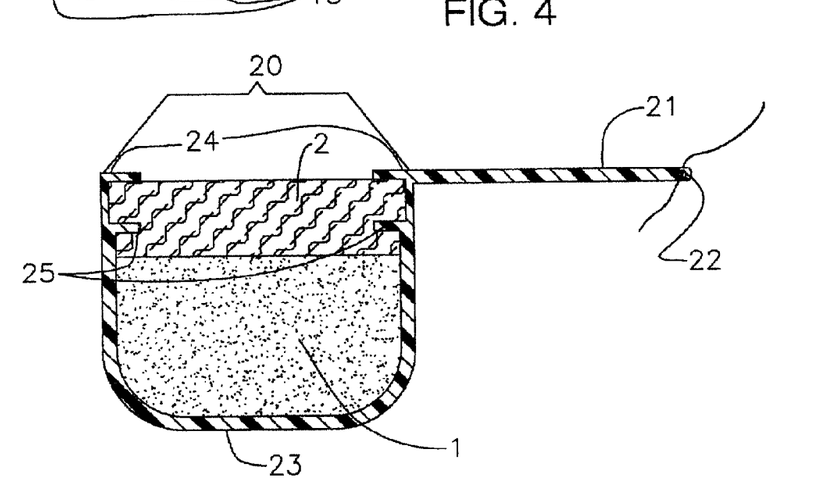
FIG. 4 of the present invention is an enlarged cross-sectional view down the center of another embodiment of the sustained release drug delivery device showing a unitary cup with a plurality of lips and an integral suture tab, a permeable plug, the cup and plug acting as a reservoir for the drug core.

FIG. 4 is a enlarged cross sectional view of a drug delivery device in accordance with the present invention. FIG. 4 includes an impermeable unitary cup 23 containing a drug core 1 comprising an agent, the cup 23 has lips 24, 25 extending inward around the open top end 20 of the cup 23; and a permeable plug 2 formed of a material permeable to the passage of agent contained in the drug core 1. The permeable plug 2 is positioned in the recess between the top of the drug core 1 and the second lip 24 such that the lips 24, 25 interact with the permeable plug 2 holding it in position and closing the open top end 20 of the cup 23.

The cup 23 further comprises an integral suture tab 21 with a hole 22 through the proximal end through which a suture can be placed to anchor the device to a structure of the organism requiring treatment. The proximal end of the suture tab is at the point of attachment, i.e. the point where the suture is attached. The preferred point of attachment is at the end of the suture tab opposite the cup.

The location of the suture and the structure the device is sutured to can be any that meet with current surgical techniques known in the art, such as the sclera of the eye. Depending upon the location of administration, the devices of the current invention may not require suturing in position.

Making the cup and suture tab in a single unitary design provides structural integrity to the device, and facilitates manufacturing and handling as one integral structure. In addition, by eliminating the assembly step of attaching the suture tab onto the cup, the single unitary design decreases variability in the size and shape of the device.

Providing a suture hole 22 at the proximal end of the suture tab of the device enables the surgeon to attach the device without additional steps. Providing the suture hole reduces the possibility of tearing the tab while passing the needle through during surgery. Some materials, such as cured polyvinyl alcohol, are also very difficult to create a suture hole in once the device is assembled without causing cracks or breaks in the suture tab.

The devices of the present invention may comprise a plurality of lips. These lips can be on the same vertical plane, as illustrated in FIG. 3, or on a different vertical plane, as illustrated in FIG. 4. The device may also be formed with any combination of lips in different vertical planes suitable to hold the permeable plug in place. For example, a single lip may be placed in the top vertical plane (position 24 in FIG. 4) and a plurality of lips, as in FIG. 3, at a lower vertical plane (position 25 in FIG. 4) positioned above the drug core to facilitate holding the permeable plug in place. The function of the lips is to hold the permeable plug in place and prevent failure of the structural integrity of the device.

The devices of the present invention that employ recessed grooves to secure the permeable plug in place may also have a plurality of grooves in the same or different vertical planes as described above.

Figure 5:
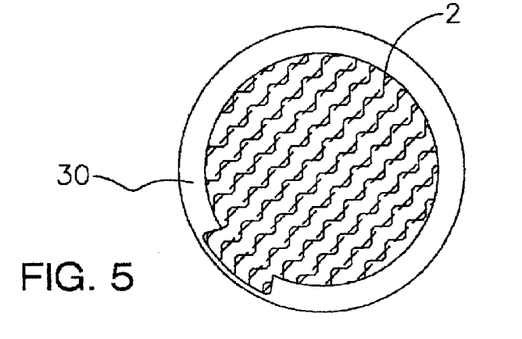
FIG. 5 is an enlarged top view of the embodiment of a sustained release drug delivery device according to the present invention showing an lip extending outward around only a portion of the open top end of the cup.

FIG. 5 is an enlarged top view of another exemplary embodiment of a sustained release drug delivery device of the present invention. The view in FIG. 5 is the top of a unitary cup comprising a single lip 30. The permeable plug 2 is held in place by the lip 30 extending inwardly around the top open end of the cup. The single lip can extend around the entire diameter of the top open end of the cup or extend around some portion, as illustrated in FIG. 5.

Figure 6:
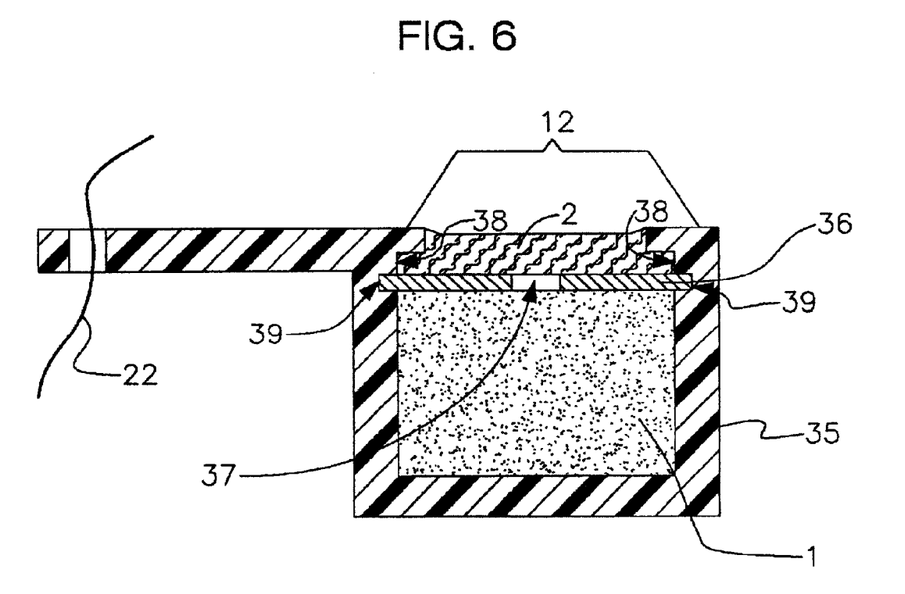
FIG. 6 of the present invention is an enlarged cross-sectional view down the center of another embodiment of the sustained release drug delivery device showing a unitary cup with a plurality of grooves and an integral suture tab, an impermeable plug with a passageway, a permeable plug, the cup and plugs acting as a reservoir for the drug core.

FIG. 6 illustrates an enlarged cross sectional view down the center of a sustained release drug delivery device in accordance with the present invention. FIG. 6 includes an impermeable unitary cup 35 containing a drug core 1 comprising an agent, the cup 35 has a plurality of grooves 38,39 around the inside of the open top end 40 of the cup 35; an impermeable plug 36 with a passageway 37, and a permeable plug 2 formed of a material permeable to the passage of agent contained in the drug core 1. The impermeable plug 36 is positioned such that the groove 39 interacts with the impermeable plug 36 holding it in position. The permeable plug 2 is positioned such that the groove 38 interacts with the permeable plug 2 holding it in position and closing the open top end 40 of the cup 35. Glue or other adhesion means can be employed to further bond the plugs to each other or the cup.

The impermeable plug of the embodiment in FIG. 6, can interact with a groove, as illustrated, or be the same radial extent as the cup. An expanded recess groove could retain the impermeable plug and still provide an anchor groove for the permeable plug.

The impermeable plug can also be utilized in this manner in the unitary cup design that comprises a lip or lips. Due to elastic nature of some polymers, such as silicone, the same result could be achieved by essentially molding the impermeable plug as part of the unitary cup and stretching the passageway wide enough to insert the tablet or filling in a liquid or powder drug core through the passageway.

In combination with the examples above, a variety of methods may also be utilized to provide adhesion of the permeable plug to the unitary cup portion of the device. These methods include the use of adhesives, polymers such as PVA, or any other procedure known in the art to provide adhesion at the points of contact between the permeable plug and the unitary cup. The sealant can be permeable or impermeable to the agent or agents in the device depending upon the method and location of application. If the adhesive is permeable to the beneficial agent, such as in the case of a permeable polymer, it could be applied on top of the drug core or directly to the permeable plug. The methods to improve adhesion will vary depending on the materials that the components are manufactured from.

The above-described methods of adhesion may also be utilized to provide adhesion of the impermeable plug to the unitary cup or permeable plug. For example, impermeable adhesives could be applied to only the edges of the impermeable plug and because the adhesive is present only on the edges, it improves the bond between the impermeable plug and the device without interfering with diffusion through the passageway(s) and the permeable plug. If the adhesive is permeable to the beneficial agent, such as in the case of a permeable polymer, it could be applied on top of the drug core, on top of the impermeable plug, or directly to the impermeable plug before the impermeable plug is put into place.

The drug core or reservoir contains an agent effective in obtaining a desired local or systemic physiological or pharmacological effect. The following classes of agents could be incorporated into the devices of the present invention: anesthetics and pain killing agents such as lidocaine and related compounds and benzodiazepam and related compounds; anti-cancer agents such as 5-fluorouracil, adriamycin and related compounds; anti-fungal agents such as fluconazole and related compounds; anti-viral agents such as trisodium phosphomonoformate, trifluorothymidine, acyclovir, ganciclovir, DDI and AZT; cell transport/mobility impending agents such as colchicine, vincristine, cytochalasin B and related compounds; antiglaucoma drugs such as beta-blockers: timolol, betaxolol, atenalol, etc; antihypertensives; decongestants such as phenylephrine, naphazoline, and tetrahydrazoline; immunological response modifiers such as muramyl dipeptide and related compounds; peptides and proteins such as cyclosporin, insulin, growth hormones, insulin related growth factor, heat shock proteins and related compounds; steroidal compounds such as dexamethasone, prednisolone and related compounds; low solubility steroids such as fluocinolone acetonide and related compounds; carbonic anhydrize inhibitors; diagnostic agents; antiapoptosis agents; gene therapy agents; sequestering agents; reductants such as glutathione; antipermeability agents; antisense compounds; antiproliferative agents; antibody conjugates; antidepressants; bloodflow enhancers; antiasthmatic drugs; antiparasiticagents; non-steroidal anti inflammatory agents such as ibuprofen; nutrients and vitamins: enzyme inhibitors; antioxidants; anticataract drugs; aldose reductase inhibitors; cytoprotectants; cytokines, cytokine inhibitors and cytokin protectants; uv blockers; mast cell stabilizers; and anti neovascular agents such as antiangiogenic agents like matrix metalloprotease inhibitors.

Examples of such agents also include neuroprotectants such as nimodipine and related compounds; antibiotics such as tetracycline, chlortetracycline, bacitracin, neomycin, polymyxin, gramicidin, oxytetracycline, chloramphenicol, gentamycin, and erythromycin; antiinfectives; antibacterials such as sulfonamides, sulfacetamide, sulfamethizole, sulfisoxazole; nitrofurazone, and sodium propionate; antialler genics such as antazoline, methapyriline, chlorpheniramine, pyrilamine and prophenpyridamine; anti-inflammatories such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone and triminolone; miotics and anti-cholinesterase such as pilocarpine, eserine salicylate, carbachol, di-isopropyl fluorophosphate, phospholine iodine, and demecarium bromide; mydriatics such as atropine sulfate, cyclopentolate, homatropine, scopolamine, tropicamide, eucatropine, and hydroxyamphetamine; sympathomimetics such as epinephrine; and prodrugs such as those described in Design of Prodrugs, edited by Hans Bundgaard, Elsevier Scientific Publishing Co., Amsterdam, 1985. In addition to the above agents, other agents suitable for treating, managing, or diagnosing conditions in a mammalian organism may be placed in the inner core and administered using the sustained release drug delivery devices of the current invention. Once again, reference may be made to any standard pharmaceutical textbook such as Remington's Pharmaceutical Sciences for the identity of other agents.

Any pharmaceutically acceptable form of such a compound may be employed in the practice of the present invention, i.e., the free base or a pharmaceutically acceptable salt or ester thereof. Pharmaceutically acceptable salts, for instance, include sulfate, lactate, acetate, stearate, hydrochloride, tartrate, maleate and the like.

A large number of polymers can be used to construct the devices of the present invention. The only requirements are that they are inert, non-immunogenic and of the desired permeability. Materials that may be suitable for fabricating the device include naturally occurring or synthetic materials that are biologically compatible with body fluids and body tissues, and essentially insoluble in the body fluids with which the material will come in contact. The use of rapidly dissolving materials or materials highly soluble in body fluids are to be avoided since dissolution of the wall would affect the constancy of the drug release, as well as the capability of the device to remain in place for a prolonged period of time.

Naturally occurring or synthetic materials that are biologically compatible with body fluids and eye tissues and essentially insoluble in body fluids which the material will come in contact include, but are not limited to, glass, metal, ceramics, polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, plasiticized ethylene vinylacetate copolymer, polyvinyl alcohol, polyvinyl acetate, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly (1,4'-isopropylidene diphenylene carbonate), vinylidene chloride, acrylonitrile copolymer, vinyl chloride-diethyl fumerale copolymer, butadiene/styrene copolymers, silicone rubbers, especially the medical grade polydimethylsiloxanes, ethylene-propylene rubber, silicone-carbonate copolymers, vinylidene chloride-vinyl chloride copolymer, vinyl chloride-acrylonitrile copolymer and vinylidene chloride-acrylonitride copolymer.

The device can be formulated in any convenient shape. For example, the device can be of any geometric shape dimensionally suitable for insertion in the eye. Thus, the device can be ellipsoid, rectangular, round, etc. The shape of the cup in the present can be optimized to provide a minimum profile for insertion.

The dimensions of the device can vary with the size of the device, the size of the core or reservoir, and the membrane that surrounds the core or reservoir. The targeted disease state, type of mammalian organism, location of administration, and agents or agent administered are among the factors which would effect the desired size of the sustained release drug delivery device.

The device according to the present invention may be made in a variety of ways. For example, if the unitary cup is going to be made entirely of polymer, then the polymer can be injection molded or die cast into a desired shape and size. The permeable plug can also be formed by any conventional means depending on the materials selected. For example, the permeable plug can be formed by injecting, pouring, adding drop wise, or molding the permeable material. Depending on the permeable material chosen, it may be required to dry and/or be cured to form the plug. The agent can be filled into the reservoir by any conventional means such as drop-wise, syringe, or pipette. The agent can also be made as a solid dose form such as a tablet or pellet and placed into the unitary cup. For example, a standard size tablet could be used with varying compositions.

The preceding descriptions of how to make the device of the present invention is merely illustrative and should not be considered as limiting the scope of the invention in any way. In particular, the methods of making the device depend on the identity of the agent.

The devices may be surgically implanted at or near the site of action. This is the case for devices of the present invention used in treatment of ocular conditions, primary tumors, rheumatic and arthritic conditions, and chronic pain. The devices may also be implanted subcutaneously, intramusclarly, intraarterially, or intraperitoneally. This is the case when devices are to give sustained systematic levels and avoid premature metabolism. In addition, such devices may be administered orally.

Once in place, the device functions as a drug reservoir gradually releasing drug to the organ such as the eye and surrounding tissue. This device is particularly useful for treating ocular conditions such as glaucoma, proliferative vitreoretimopathy, diabetic retinopathy, uveitis, and keratitis. The device is also particularly useful as an ocular device in treating mammalian organisms suffering from cytomegalovirus retinitis wherein the device is surgically implanted within the vitreous of the eye.

As would be readily understood by one skilled in the art, the preferred amounts, materials, and dimensions depend on the method of administration, the effective agent used, the polymers used, the desired release rate and the like. Likewise, actual release rates and release duration depend on a variety of factors in addition to the above, such as the disease state being treated, the age and condition of the patient, the route of administration, as well as other factors which would be readily apparent to those skilled in the art. All of the forgoing U.S. Patents and other publications are expressly incorporated by reference herein in each of their entities.

Thus, the devices of the present invention provide many important advantages over previously known sustained release drug delivery devices. The unitary cup and plug design of the present invention provide an improved device that maintains its physical and chemical integrity in both the environments of use and in the presence of agent during the controlled and continuous dispensing of agent over a prolonged period of time.

Forming the permeable plug in the unitary cup enables superior interaction with the lips or grooves of the unitary cup thereby locking the permeable plug in place. The resulting device has superior structural stability under the conditions of use.

Because of the structural integrity of the present design, the need for coatings and multiple layers can be eliminated. For transport of agent out of the device and into the target area, it is only necessary that the permeable layer cover the portions of the device not covered with the impermeable layer.

The unitary cup design and the use of plugs of the present invention result in a device that is more easily and reproducibly manufactured then current designs known in the art. Manufacturing with the single unitary cup and plugs minimizes the number of steps and decreases potential variability in assembly. The present design also allows for mechanized manufacture. Eliminating manual assembly greatly decreases the potential variability in the finished product.

Another advantage of the devices of the present invention is the ease of construction by more standard manufacturing techniques into devices with different release rates. The passageway in the impermeable plug allows for release of the agent. A single standard cup size can be used for multiple dosage configurations by varying the size or number of passageways in the impermeable plug, or by not using the impermeable plug at all. The permeable plug can also be made to various dimensional specifications that can be used to control diffusion properties to achieve a desired release rate. Thus, the same unitary cup can be used for implants with different release rates making it possible to use a single manufacturing line or type of equipment.

In addition, the use of a single unitary cup and permeable plug to form the container or drug reservoir of the present design provides more consistent and improved sealing capacity over the devices in the prior art. This permits the therapeutic program to be precisely controlled and the release of drug to be constant and predicted with accuracy.

The ease of making the devices in the present invention minimizes stresses, strains, and deformations of the devices during manufacture which may cause the reservoir to rupture and leak. The leaking of agent can result in harm to the patient and is a significant concern in the manufacture of implantable devices.

The following specific examples demonstrate sustained release drug delivery device designs of the present invention. However, it is to be understood that these examples are for illustrative purposes only and do not purport to be wholly definitive as to the conditions and scope.

EXAMPLE 1

A device according to the present invention is prepared. The unitary cup is made of silicone and has eight inwardly extending lips around the top open end of the cup. The unitary cup has an integral suture tab with a hole at the end of the tab opposite the cup. The drug core is formed as a pellet composed of a 2.5 mg core of fluocinolone acetonide and inserted into the cup. A 10% PVA solution is injected into the unitary cup filling the recess between the drug core and the lips. The PVA is allowed to dry. The device is cured at 135–140° C. for 50 minutes. The lips act to hold the permeable plug in place.

EXAMPLE 2

The device of example 1 above is placed in a vial with 2.0 mL of a release media of 0.1 Sodium Acetate, pH 4.2. The vial is maintained in a 37° C. bath for 24 hours. After 24 hours, the vial is inverted to ensure homogeneity and the device is removed to a new vial with fresh media. This process is repeated for each day. The media is tested to determine the amount of the drug and verifies that it is being released from the device. From the data that is collected, the release rate of the device can be determined.

EXAMPLE 3

A device according to the present invention is prepared. The unitary cup is made of silicone and has two recessed grooves, one above the other, around the inside of the top open end of the cup. The first groove, which is the one further from the top open end of the cup, is deeper then the second groove. The unitary cup has an integral suture tab with a hole at the end of the tab opposite the cup for suturing the device to a structure of a mammalian organism. The drug core is formed as a tablet composed of a 0.5 mg core of fluocinolone acetonide and inserted into the cup. An impermeable plug made of silicone, with a passageway in the center, is placed in the cup fitting into the first groove. A 10% PVA solution is filled into the unitary cup filling in the recess above the impermeable plug. The PVA is allowed to dry. The device is cured at about 140° C. for 50 minutes. The second groove interacts with the permeable plug holding it in place.

From the foregoing description, one of ordinary skill in the art can easily ascertain the essential characteristics of the instant invention, and without departing from the spirit and scope thereof, can make various changes and/or modifications of the inventions to adapt it to various usages and conditions. As such, these changes and/or modifications are properly, equitably, and intended to be, within the full range of equivalence of the following claims.

What is claimed is:

1. A sustained release drug delivery device comprising:
   a) a drug core comprising a therapeutically effective amount of at least one agent effective in obtaining a diagnostic effect or effective in obtaining a desired local or systemic physiological or pharmacological effect;
   b) a unitary cup essentially impermeable to the passage of said agent that surrounds and defines an internal compartment to accept said drug core, said unitary cup comprising an open top end with at least one recessed groove around at least some portion of said open top end of said unitary cup wherein said unitary cup further comprises an integral suture tab; and
   c) a permeable plug which is permeable to the passage of said agent, said permeable plug is positioned at said open top end of said unitary cup wherein said groove interacts with said permeable plug holding it in position and closing said open top end, said permeable plug allowing passage of said agent out of said drug core, through said permeable plug, and out said open top end of said unitary cup.

2. The sustained release drug delivery device according to claim 1, wherein said unitary cup is made of polymer or metal.

3. The sustained release drug delivery device according to claim 1, wherein said integral suture tab has a hole through the proximal end through which a suture can be planed to anchor the device to a structure.

4. The sustained release drug delivery device according to claim 1, wherein said unitary cup is made of silicone.

5. The sustained release drug delivery device according to claim 4, wherein said permeable plug is made of PVA.

6. The sustained release drug delivery device according to claim 1, wherein said unitary cup further comprises a plurality of recessed grooves around at least some portion of said open top end of said unitary cup.

7. The sustained release drug delivery device according to claim 1, wherein said agent is a low solubility agent.

8. The sustained release drug delivery device according to claim 1, wherein said agent is selected from a group consisting of immune response modifiers, neuroprotectants, corticosteroids, angiostatic steroids, anti-parasitic agents, anti-glaucoma agents, anti-biotics, ant-sense compounds, anti-angiogenic compounds, differentiation modulators, anti-viral agents, anti-cancer agent, and nonsteroidal anti-inflammatory agents.

9. The sustained release drug delivery device according to claim 1, wherein said drug core comprises a plurality of agents.

10. The sustained release drug delivery device according to claim 1, further comprising an impermeable plug with at least one passageway positioned between said drug core and said permeable plug.

11. A sustained release drug delivery device comprising:
   a) a drug core comprising at least one agent effective in obtaining a diagnostic effect or effective in obtaining a desired local or systemic physiological or pharmacological effect;
   b) a unitary cup essentially impermeable to the passage of said agent that surrounds and defines an internal compartment to accept said drug core, said unitary cup comprising an open top end and at least one lip around at least a portion of said open top end of said unitary cup wherein said unitary cup further comprises an integral suture tab; and c) a permeable plug permeable to the passage of said agent positioned at said open top end of said unitary cup wherein said lip interacts with said permeable plug holding it in position and closing said open top end, said permeable plug allowing passage of said agent out of said drug core, through said permeable plug, and out said open top end of said unitary cup.

12. The sustained release drug delivery device according to claim 11, wherein said lip extends around the entirety of said open top end of said unitary cup.

13. The sustained release drug delivery device according to claim 11, wherein said unitary cup comprises a plurality of lips at said open top end of said unitary cup.

14. The sustained release drug delivery device according to claim 11, wherein said drug core comprises an effective amount of a low solubility agent.

15. The sustained release drug delivery device according to claim 11, wherein said agent is selected from a group consisting of immune response modifiers, neuroprotectants, corticosteroids, angiostatic steroids, anti-parasitic agents, anti-glaucoma agents, anti-biotics, anti-sense compounds, anti-angiogenic compounds, differentiation modulators, anti-viral agent, anti-cancer agents, and nonsteroidal anti-inflammatory agents.

16. The sustained release drug delivery device according to claim 11, wherein said unitary cup is made of polymer or metal.

17. The sustained release drug delivery device according to claim 11, wherein said unitary cup is made of silicone.

18. The sustained release drug delivery device according to claim 17, wherein said permeable plug is made of PVA.

19. The sustained release drug delivery device according to claim 11, wherein said suture tab has a hole through the proximal end through which a suture can be placed to anchor the device to a structure.

20. The sustained release drug delivery device according to claim 11, wherein said drug core comprises a plurality of agents.

21. The sustained release drug delivery device according to claim 11, further comprising an impermeable plug with at least one passageway positioned between said drug core and said permeable plug.

22. A method for providing controlled and sustained administration of an agent effective in obtaining a desired local or systemic physiological or pharmacological effect comprising inserting in a desired location in the body of a mammalian organism a sustained release drug delivery device comprising:

a) a drug core comprising a therapeutically effective amount of at least one agent effective in obtaining a diagnostic effect or effective in obtaining a desired local or systemic physiological or pharmacological effect;

b) a unitary cup essentially impermeable to the passage of said agent that surrounds and defines an internal compartment to accept said drug core, said unitary cup comprising an open top end with at least one recessed groove around at least some portion of said open top end of said unitary cup wherein said unitary cup further comprises an integral suture tab; and c) a permeable ping which is permeable to the passage of said agent positioned at said open top end of said unitary cup wherein said groove interacts with said permeable plug holding it in position and closing said open top end, said permeable plug allowing passage of said agent out of said drug core, through said permeable plug, and out said open top end of said unitary cup.

23. The method according to claim 22, wherein said inserting step comprises inserting said sustained release drug device in a location selected from a group consisting of the vitreous of the eye, under the retina, and onto the sclera.

24. The method according to claim 22, wherein said drug core comprises a plurality of agents.

25. The method according to claim 22, wherein said inserting step comprises injecting said sustained release drug delivery device at the desired location.

26. A method for providing controlled and sustained administration of an agent effective in obtaining a desired local or systemic physiological or pharmacological effect comprising inserting at a desired location in the body of a mammalian organism a sustained release drug delivery device comprising;

a) a drug core comprising at least one agent effective in obtaining a diagnostic effect or effective in obtaining a desired local or systemic physiological or pharmacological effect;

b) a unitary cup essentially impermeable to the passage of said agent that surrounds and defines an internal compartment to accept said drug core, said unitary cup comprising an open top end and at least one lip around at least a portion of said open top end of said unitary cup wherein said unitary cup further comprises an integral suture tab; and c) a permeable plug permeable to the passage of said agent positioned at said open top end of said unitary cup wherein said lip interacts with said permeable plug holding it in position and closing said open top end, said permeable plug allowing passage of said agent out of said drug core, through said permeable plug, and out said open top end of said unitary cup.

27. The method according to claim 26, wherein said inserting step comprises inserting said sustained release drug delivery device in a location selected from a group consisting of the vitreous of the eye, under the retina, and onto the sclera.

28. The method according to claim 26, wherein said drug core contains a plurality of said agents.

29. The method according to claim 26, wherein said inserting step comprises injecting said sustained release drug delivery device at the desired location.

30. A method of manufacturing a sustained release drug delivery device comprising:

a) manufacturing a drug core comprising at least one agent effective in obtaining a diagnostic effect or effective in obtaining a desired local or systemic physiological or pharmacological effect;

b) providing a unitary cup essentially impermeable to the passage of said agent that surrounds and defines an internal compartment to accept said drug core, said unitary cup comprising an open top end with at least one recessed groove around at least some portion of said open top end of said unitary cup wherein said unitary cup further comprises an integral suture tab;

c) inserting said drug core into said unitary cup; and d) filling a material which is permeable to the passage of said agent into said open top end of said unitary cup, allowing said material to solidify thereby forming a permeable plug positioned at said open top end of said unitary cup wherein said groove interacts with said permeable plug holding it in position and closing said open top end, said permeable plug allowing passage of said agent out of said drug core, through said permeable plug, and out said open top end of said unitary cup.

31. The method of manufacturing a sustained release drug delivery device according to claim 30, wherein said drug core is manufactured as a solid dose form.

32. The method of manufacturing a sustained release drug delivery device according to claim 30, wherein said drug core is manufactured as a solid dispersion.

33. The method of manufacturing a sustained release drug delivery device according to claim 30, comprising the further step of curing the assembled sustained release drug delivery device.

34. A method of manufacturing a sustained release drug delivery device comprising:
   a) manufacturing a drug core comprising at least one agent effective in obtaining a diagnostic effect or effective in obtaining a desired local or systemic physiological or pharmacological effect;
   b) providing a unitary cup essentially impermeable to the passage of said agent that surrounds and defines an internal compartment to accept said drug core, said unitary cup comprising an open top end with at least one lip extending around at least a portion of the said open top end of said unitary cup wherein said unitary cut further comprises an integral suture tab;
   c) inserting said drug core into said unitary cup; and
   d) filling a material which is permeable to the passage of said agent into said open top end of said unitary cup, allowing amid material to solidify thereby forming a permeable plug positioned at said open top end of said unitary cup wherein said lip interacts with said permeable plug holding it in position and closing said open top end, said permeable plug allowing passage of said agent out of said drug core, through said permeable plug, and out said open top end of said unitary cup.

35. The method of manufacturing a sustained release drug delivery device according to claim 34, wherein said drug core is manufactured as a solid dose form.

36. The method of manufacturing a sustained release drug delivery device according to claim 34, wherein said drug core is manufactured as a solid dispersion.

37. The method of manufacturing a sustained release drug delivery device according to claim 34, comprising the further step of curing the assembled sustained release drug delivery device.

* * * * *